United States Patent [19]

Leman et al.

[11] 4,080,501

[45] Mar. 21, 1978

[54] MELAMINE PHOSPHATE

[75] Inventors: Jeffrey Donald Leman, Montreal; Allan James Robertson, Niagara, both of Canada

[73] Assignee: American Cyanamid Company, Stamford, Conn.

[21] Appl. No.: 372,121

[22] Filed: Jun. 21, 1973

[51] Int. Cl.² ........................................... C07D 251/70
[52] U.S. Cl. .................................... 544/195; 252/8.1; 156/103; 106/15 FP
[58] Field of Search ...................... 260/249.6; 544/195

[56] References Cited

U.S. PATENT DOCUMENTS

| | | | |
|---|---|---|---|
| 3,284,216 | 11/1966 | Kaplan | 260/249.6 |
| 3,296,265 | 1/1967 | Garner | 260/249.6 |

OTHER PUBLICATIONS

Barr et al., Chem. Reviews, vol. 58, No. 1, pp. 135–136 (Feb. 1958).

*Primary Examiner*—John M. Ford
*Attorney, Agent, or Firm*—Frank M. Van Riet

[57] ABSTRACT

Melamine phosphate having hydrogen bonded thereto from about 0.5 to about 1.5 moles of phosphoric acid per mole of melamine phosphate, particleboard containing said melamine phosphate material and processes for the production thereof, are disclosed.

5 Claims, No Drawings

MELAMINE PHOSPHATE

BACKGROUND OF THE INVENTION

Due to the increasing demand for particleboard in the building industry and the requirements that all building materials conform to stringent standards of flame-retardancy, efforts to develop a particleboard which may be used in most building environments have recently been initiated. Many additives have been incorporated into particleboard to render it fire-retardant, but the most widely accepted additives each have some feature which is not desired but is tolerated. Some of the most widely used additives must be used in very large concentrations before acceptable boards can be produced while others must be added to the wood chips as liquid solutions which requires expensive drying thereof before the particleboard can be manufactured. Other additives tend to leach out of the particleboard when in contact with water while others do not produce Class I boards no matter how much additive is used.

SUMMARY OF THE INVENTION

It has now been disclosed that melamine phosphate having phosphoric acid hydrogen bonded thereto and which is produced according to certain well defined conditions, can be incorporated into wood particleboard as a solid, will impart flame-retardance to the board and will not leach out of the board during use since it is substantially water-insoluble. The use of the novel melamine phosphate-phosphoric acid material obviates various drying procedures usually necessary in commercial procedures wherein the fire-retardant is applied as a solution.

BACKGROUND OF THE INVENTION INCLUDING PREFERRED EMBODIMENTS

As mentioned above, it has now been found that wood particleboard can now be made fire-resistant by the incorporation of a novel melamine phosphate-phosphoric acid material therein. This melamine phosphate-phosphoric acid material melts over a wide temperature range and has been found to impart a higher degree of fire-retardancy to wood particle-board than pure melamine phosphate per se.

The melamine phosphate-phosphoric acid material of the instant invention is produced by reacting phosphoric acid with melamine at a molar ratio of at least about 1.5:1, respectively, preferably from about 1.5–2.5:1, respectively. The product is recovered in the form of an off-white powder having a bulk density of 46.5 lb./ft.$^3$ and an angle of repose of 54°. It has a melting point range of from about 278°–386° C. with decomposition and is very slightly soluble in water. The melamine phosphate-phosphoric acid material of the instant invention is stable indefinitely under ordinary conditions and is non-flammable.

The novel melamine phosphate-phosphoric acid material of this invention may be produced by adding one mole of melamine to a suitable blending vessel containing at least about 1.5 mole of phosphoric acid (an 85% solution in water is usually employed). The mixture is then violently agitated for from about 15 seconds to 5 minutes and the resultant product is recovered by pouring the reaction media onto a solid surface and allowing it to solidify, usually in from about 2–10 minutes. The solid mass is then dried overnight at 110° C. and pulverized to the desired consistency.

A second method of production which has been found to be useful is to add one mole of melamine to about one mole of the aqueous phosphoric acid medium and then stir the mixture as above. The precipitate which forms is filtered and oven dried overnight at 110° C. The resultant dried material is then blended with additional phosphoric acid e.g. 0.5–1.5 mole and again dried overnight at 110° C.

It is preferred to add the melamine to the phosphoric acid but this order of addition is not critical and may be reversed if desired. Additionally, it is not critical that the entire amount of either component be added at once i.e. 0.5 mole of melamine (or any concentration thereof) may be added to 1.0 mole of phosphoric acid (or any concentration thereof) and then additional melamine or phosphoric acid can be added to the resultant reaction product, before or after drying, to bring the reactant concentrations within the range, above specified.

All of these procedures have been found to result in a unique melamine phosphate-phosphoric acid product which imparts excellent flame-retardance to wood particleboard when applied thereto.

The exact chemical structure of the melamine phosphate-phosphoric acid material of the present invention is not known with certainty, however, it appears to be more closely a combination of melamine phosphate and phosphoric acid with the excess phosphoric acid which does not enter into the melamine phosphate production being hydrogen bonded thereto.

While not wishing to be bound to any particular theory or structure with regard to our melamine phosphate-phosphoric acid material, it is believed that the material can be presented structurally thusly;

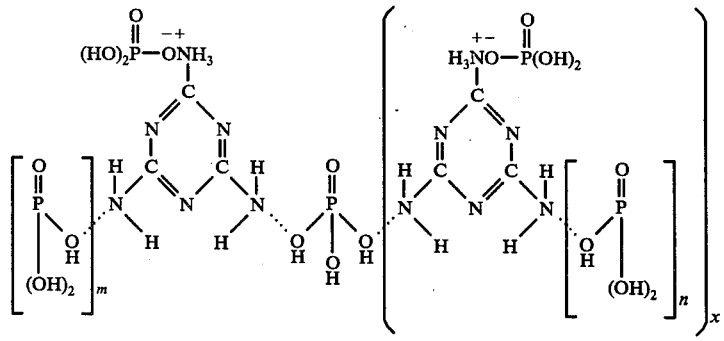

wherein $m$ is an integer of 0–1, inclusive, $n$ is an integer of 0–1, inclusive, $x$ is an integer of 0–1, inclusive, and when $x=0$, $m=0$.

The novel particleboard of this invention exhibits a high degree of flame-retardance, as mentioned above, and can be produced according to any known procedure. For example, the multi-platen process, the extrusion process, the continuous pressing process or any other known process may be used, especially those taught by The Wood Particle Board Handbook, Carlyle et al, Published by The Industrial Experimental Program of the School of Engineering, North Carolina State College, Raleigh, North Carolina, August, 1956, which is hereby incorporated herein by reference.

The flame-retardant melamine phosphate-phosphoric acid material may be added to the wood chips from which the particle-board is to be produced before, during or after the application of the glue thereto. It should be applied in such concentrations that at least about 2%, by weight, preferably from about 10% to about 30%, by weight, of the particleboard, contains the phosphate-hydrogen bonded phosphoric acid material. The material can be added as such, but it is preferred that small amounts i.e. up to about 2.0%, by weight, of a fluidizing agent such as silica, talc, clay, diatomaceous earth etc. be added thereto in order to increase the flow properties thereof.

It is also preferred that the melamine phosphate-phosphoric acid mixture be utilized as particles of less than about 28 Tyler mesh in order that it may be more easily handled and incorporated into the particleboard.

The melamine phosphate-phosphoric acid material is incorporated into the particleboard by treating the chips from which the wood is to be made before consolidation thereof. The preferred method is to spray or otherwise contact the chips with the melamine phosphate-phosphoric acid material powder in order to coat the chips with the powder i.e. the powder clings to the wood fibers and is retained thereon. The coated wood chips are then sprayed or otherwise contacted with the appropriate glue and the resultant chips are heat and pressure consolidated into the particleboard after they have been placed in an appropriately shaped mold or press.

The glue may be added to the wood chips before the solid melamine phosphate but this order of addition tends to cause the phosphate particles to clump together and thereby coat the chips in a non-uniform manner. The same result occurs if the glue and the melamine phosphate are applied simultaneously.

Example of suitable glues which can be used include melamine/formaldehyde resins, urea/formaldehyde resins, phenolic resins, organic glues, animal glues, lignin, mixtures of these and other glues and the like, with the resinous glues and mixtures thereof being preferred.

The particleboard of the instant invention can be uni-layer or multi-layer products and the flame-retardant melamine phosphate-phosphoric acid material can be added to all layers or only to the surface layer of the particleboard to render it flame-resistant. It is preferred that when multilayered boards are produced, the flame-retardant be placed only in the surface layers. In multi-layered boards the two outer surfaces are usually prepared from wood chips having a size ranging from about 15 Tyler mesh to about 150 Tyler mesh while the core is produced from wood chips having a size ranging from about 8 Tyler mesh to about 14 Tyler mesh.

For purposes of this specification and as used herein, the term "particleboard" is meant to include all boards prepared from wood chips or particles regardless of whether the ultimate product is referred to as chipboard, flakeboard or the like.

Appropriate combinations of glue and the melamine phosphate-phosphoric acid flame-retardant can be used so as to render the resultant board both fire-retardant and water-resultant, the water-resistance being imparted to the particle-board primarily by the glue, as is known in the art.

The type of wood employed in the production of the novel particleboard of this invention is not critical and such woods as pine, aspen, spruce, hemlock, ash, oak etc. can be used each adding its own particular characteristics to the resultant product.

Generally, the core of multi-layered particleboard accounts for from about 50% to about 80% of the total board weight with the surface layers accounting for from about 20% to about 50%, thereof.

The following examples are set forth for purposes of illustration only and are not to be construed as limitations on the present invention except as set forth in the instant claims. All parts and percentages are by weight unless otherwise specified.

In the following examples, the Flame Spread Ratings are determined with a Pittsburg-Corning 30"/30° Flame Spread Tunnel which was correlated with the Underwriter's Laboratory of Canada 25 foot tunnel ASTM E84–68. On a scale based on asbestos with a Flame Spread Rating of 0 and red oak with a Flame Spread Rating of 100, particleboards with Flame Spread Ratings of 25 or less are designated as Class I boards, Flame Spread Ratings of 26–75 are designated Class II boards and ratings of 76–150 are designated as Class III products. Repeated testing indicates that Flame Spread Ratings can be obtained from the Pittsburg-Corning tunnel with an accuracy of ± 2.0 unit in the Class I range. In the upper Class II range, this accuracy is reduced.

The particleboards produced in the following examples are of two sizes, i.e. 6 inches × 6 inches and 18 ¾ inches × 14 inches and are of three layer construction unless otherwise indicated. The two surface layers are formed of wood chip mixtures of about 15–150 Tyler mesh in size while the core layer utilizes chip mixtures of about 8–14 Tyler mesh in size. The boards have 20 weight percent chips and glue in the surface layers. The amount of chips and glue needed to make any given size board is readily calculatable depending on the thickness and density of the board required. These calculations are well known to those skilled in the art and need not be further elaborated upon herein.

For laboratory testing, the required amount of core chips is weighed out in a suitable vessel and charged to a suitable agitation vessel modified with a spray nozzle for glue application and an inlet for fire-retardant to be applied as a solid. The core chips are then sprayed with the appropriate amount of glue while they are being agitated. After spraying, the chips and glues are allowed to mix for an additional 3–4 minutes and are then discharged. The surface chips are then contacted with the solid flame-retardant and the glue is then mixed in similarly.

A Teflon ® treated stainless steel plate having an appropriately sized wooden frame thereon is then placed on a scale and the first surface layer of glue and flame-retardant treated chips are weighed out and spread inside the frame and onto the plate. The core chips are then also weighed out and spread atop the first surface layer, followed by a second surface layer similar to the first. The chips and glue are then somewhat compacted and the wooden frame is removed leaving a particleboard mat around which there is then placed a steel stop whose thickness is the same as that intended for the final board. A second Teflon ® treated plate is then placed on top of the mat and the entire assembly is placed on the bottom heater plate of a hydraulic press. The mat is then compressed to the thickness of the stop, heated and cured until the glue sets. The plates and stop are then removed from the press and the particleboard recovered. The length of time and temperature required to properly cure the particleboard depends upon the glue used and the board thickness.

In detecting water-resistance, a two hour boil test is used wherein 2 inches × 2 inches board samples are placed in boiling water for two hours and then removed, dried and measured. If an increase in thickness of more than about 20–30% is shown, the samples are not considered to be water-resistant.

EXAMPLE 1

A. One mole of melamine is added to a suitable blending vessel containing 1.6 mole of 85% phosphoric acid and the mixture is violently agitated for thirty seconds. The resulting product is poured onto a stainless steel plate, allowed to solidify, about 5 minutes, and then oven dried overnight at 110° C. The dried material is then pulverized.

B. One mole of melamine is added to an aqueous phosphoric acid medium (1.05 mole) in an agitation vessel and the mixture is stirred for several minutes. The product which precipitates is filtered and oven dried overnight at 110° C. The dried material is then blended with additional phosphoric acid (85%; 0.6 mole) and the product is dried in an oven overnight at 110° C.

The properties of the melamine phosphate-phosphoric acid materials produced in Examples 1A and 1B, above, are set forth below.

| Appearance: | off-white powder | | |
|---|---|---|---|
| Bulk Density: | 46.5 lb./ft.$^3$ | | |
| Particle Size: | 100%-28 Tyler mesh | | |
| Angle of Repose: | 54° | | |
| Elemental Analysis: | | | |
| Nitrogen: | 29.5% | | |
| Phosphorus: | 17.4% | | |
| Melting Point: | 278–386° C. with decomposition | | |
| Solubility in H$_2$O and pH | Temp. °C | gm/100 ml solution | pH: |
| | 26 | 0.36 | 3.2 |
| | 65 | 1.76 | 3.1 |
| | 95 | 4.40 | 3.0 |

The product is stable indefinitely under normal conditions. Slight absorption of moisture may occur if left exposed to humid atmosphere.

EXAMPLE 2

In this example, the test boards are 18 inches × 14 ⅝ inches and are designed to have a density of 45 lb./ft.$^3$ at the beginning of the cure cycle. The glue is a mixture of 37.5 parts of a commercially available melamine/formaldehyde resin, 50.0 parts of a commercially available urea/formaldehyde resin and 12.5 parts of water and contains 60% glue solids. The wood chips used are aspen dried to about 5% moisture. The core chips pass through a No. 8 Tyler mesh screen but not through a No. 14 Tyler mesh screen. The surface chips pass through a No. 14 Tyler mesh screen but not through a No. 150 Tyler mesh screen.

169 Parts of the melamine phosphate-phosphoric acid material of Example 1A, containing 0.75% of a commercially available silica fluidizing agent, are added to 510 parts of surface chips in a suitable rotating vessel. 169 Parts of the glue mixture are then sprayed as an aerosol mist onto the chips. Surface chips containing 20% flame-retardant and 12% glue solids result. 1040 Parts of core chips are then sprayed with 260 parts of the glue mixture in a similar vessel. The core chips then also contain 12% glue solids.

373 Parts of the treated surface chips are laid in a wooden frame followed by 1115 parts of treated core chips. Finally, 373 additional parts of the same treated surface chips are used to form the top surface. The surface layers account for 40% of the total board weight.

The mat is cold pressed slightly with less than 0.5 p.s.i. pressure. The frame is removed and the mat is pressed to ⅝ inch thickness and is cured for 14 minutes at 260° F.

The resultant particleboard is recovered and subjected to the above described flame spread test. The Flame Spread Rating is 23.5. Without any fire-retardant, the rating is 80–90.

To test for water-resistance, 2 inch × 2 inch sections of the board are boiled for two hours in water. The percent increase in thickness after the sections are air dried overnight at room temperature is 24.7%. The internal bond on the board is 143 p.s.i. and its actual density is 43.2 lb./ft.$^3$.

EXAMPLE 3

The procedure of Example 2 is again followed except that the melamine phosphate-phosphoric acid material of Example 1B is used. Substantially identical results are obtained.

EXAMPLE 4

The procedure of Example 2 is again followed except that the boards prepared are ⅝ inch thick, have densities of 45 lb./ft.$^3$, contain 10% glue solids and varying amounts of the melamine phosphate-phosphoric acid material are added. The results are set forth below.

| Percent Phosphate-Acid In Surface Layers | Flame Spread Rating |
|---|---|
| 5.0 | 49.5 |
| 10.0 | 34.0 |
| 15.0 | 24.5 |
| 20.0 | 22.5 |
| 25.0 | 17.0 |

EXAMPLE 5

The procedure of Example 2 is again followed. The particleboards formed are three layered boards, ¾ inch thick with a density of 43 lb./ft.$^3$. The glue employed is a commercially available melamine/formaldehyde resin admixed in a 1:1 ratio in a solids bases with a commercially available urea/formaldehyde resin and is present in the board at 12% solids. The results are set forth in the table below.

| Percent Phosphate-Acid in Surface Layers | Flame Spread Rating | Passes Underwriter's Class |
|---|---|---|
| 0 | 80–90 | III |
| 2.5 | 74 | II |
| 5.0 | 68 | II |
| 10.0 | 44 | II |

-continued

| Percent Phosphate-Acid in Surface Layers | Flame Spread Rating | Passes Underwriter's Class |
|---|---|---|
| 15.0 | 32 | II |
| 17.5 | 25 | I |
| 20.0 | 23 | I |
| 22.5 | 17 | I |
| 25.0 | 13 | I |
| 30.0 | 10 | I |

EXAMPLE 6

The technique employed in Example 2 is again followed except the glues employed are varied, the boards produced are 11/16 inch thick and have densities of 43–45 lbs./ft.$^3$. The surface chips to which the melamine phosphate-phosphoric acid dust is applied, constitute 40% of the total board weight. Results are specified below.

| Test No. | 1 | 2 | 3 |
|---|---|---|---|
| Glue | Urea/formaldehyde | Melamine/formaldehyde | Melamine/formaldehyde |
|  |  | Urea/formaldehyde (3:4) | Urea/formaldehyde (3:4) |
| Glue Solids | 9.6 | 13 | 12 |
| Melamine Phosphate-Acid Concentration In Surface Layers | 17.5 | 22 | 17.5 |
| 2-Hour Boil: Thickness Increase | — | 24 | 27 |
| Flame Spread Rating: Sample A | 24 | 20 | 22 |
| Sample B | 20 | 16 | — |

EXAMPLE 7

Following the procedure of Example 1A, melamine and phosphoric acid are coreacted in varying concentrations and the resultant products are incorporated into particleboards according to the technique of Example 2 except that the boards are ¾ inch thick and are bonded with a urea/formaldehyde-melamine/formaldehyde resin mixture (1:1-solids basis) with 12% glue solids. The results are shown in the table below.

| $H_3PO_4$/Melamine Molar Ratio | Fire Retardant In Surface Layers | Flame Spread Rating (A) |
|---|---|---|
| 1.0(C) | 19% | 33 |
| 1.1(C) | 19% | 33.5 |
| 1.2(C) | 19% | 32 |
| 1.3(C) | 19% | 28.5 |
| 1.4(C) | 19% | 26 |
| 1.5 | 19% | 20.5 |
| 1.6 | 19% | 20 |
| 1.7 | 19% | 19.5 |
| 1.8 | 19% | 17 |
| 1.9 | 19% | 19 |
| 2.0 | 19% | 18 |
| 2.1 | 19% | 20 |
| 2.2 | 19% | 21 |
| 2.4 | 19% | 21 |

(A) average of four burns on two different boards
(C) comparative

Additional data regarding the above boards wherein burn weight loss, water-resistance, bond pressure and densities are specified are set forth below.

| $H_2PO_4$/Melamine Molar Ratio | Fire Retardant In Surface Layers | Wt. Loss after 4-minute burn | Thickness Increase after 2-hr. boil | Internal Bond (p.s.i.) | Board Density$_3$ (lb./ft.) |
|---|---|---|---|---|---|
| 1.0(C) | 19% | 2.50% | 10.1% | 144 | 41.7 |
| 1.1(C) | 19% | 2.38 | 11.8 | 113 | 41.9 |
| 1.2(C) | 19% | 2.16 | 10.6 | 127 | 40.8 |
| 1.3(C) | 19% | 2.00 | 11.9 | 112 | 41.3 |
| 1.4(C) | 19% | 2.02 | 14.4 | 126 | 40.3 |
| 1.5 | 19% | 2.14 | 15.3 | 135 | 43.0 |
| 1.6 | 19% | 2.06 | 16.5 | 120 | 41.4 |
| 1.7 | 19% | 1.82 | 18.3 | 116 | 38.6 |
| 1.8 | 19% | 1.80 | 17.8 | 107 | 40.3 |
| 1.9 | 19% | 1.63 | 17.6 | 130 | 40.7 |
| 2.0 | 19% | 1.65 | 17.5 | 130 | 41.5 |
| 2.2 | 19% | 1.53 | 16.8 | 118 | 39.5 |
| 2.4 | 19% | 1.80 | 17.9 | 121 | 39.7 |

(C)Comparative

EXAMPLE 8

The procedure of Example 7 is again followed except that the concentration of the flame-retardant in the surface layer is maintained at 9.5%. The results are specified below.

| $H_3PO_4$/Melamine Molar Ratio | Flame Spread Rating (A) |
|---|---|
| 1.0(C) | 44.5 |
| 1.1(C) | 47 |
| 1.2(C) | 47 |
| 1.3(C) | 44.5 |
| 1.4(C) | 44.5 |
| 1.5 | 44.5 |
| 1.6 | 44.5 |
| 1.7 | 43 |
| 1.8 | 40.5 |
| 1.9 | 42 |
| 2.0 | 39 |
| 2.2 | 39 |
| 2.4 | 32.5 |

| $H_3PO_4$/Melamine Molar Ratio | Flame Spread Rating (A) |
|---|---|
| 2.6 | 31 |

(A)average value of two burns on one board
(C)Comparative

EXAMPLE 9

The procedure of Example 2 is again followed except that the melamine phosphate-phosphoric acid flame-retardant is added to the core chips and no surface chips are applied thereto. The Flame Spread Rating of the resultant uni-layer particleboard is 25.0. The water-resistance test value is 26.3% and the density is 43.4.

EXAMPLE 10

The procedure of Example 2 is again followed except the surface chips to which have been added the melamine phosphate-phosphoric acid material are applied only to one horizontal surface of the core chips. To the other side of the core is added a commercially available decorative laminate using standard contact cement. The Flame Spread Rating of the composite is 24.0.

EXAMPLE 11

The procedure of Example 5 is again followed except that the board thickness is ⅝ inch. The boards produced are cured at 256° F. for 14 minutes after having added to the surface chips thereof varying amounts of the melamine phosphate-phosphoric acid material of Example 1B. The Flame Spread Ratings are then determined before and after the 2-hour leach resistance boil test. The results are indicated below.

| Percent Melamine Phosphate-Phosphoric Acid Material In Surface Chips | Flame Spread Rating | |
|---|---|---|
| | Before Boil | After Boil |
| 2.5 | 74.0 | 75.5 |
| 5.0 | 68.0 | 70.5 |
| 10.0 | 44.0 | 51.0 |
| 15.0 | 32.0 | 44.5 |
| 17.5 | 25.0 | 31.0 |
| 20.0 | 23.0 | 28.5 |
| 22.5 | 17.0 | 26.0 |
| 25.0 | 13.0 | 18.0 |
| 30.0 | 10.0 | 18.0 |

We claim:
1. A method for the production of melamine phosphate having hydrogen bonded thereto at least about 0.5 mole of ortho phosphoric acid per mole of melamine phosphate which comprises reacting ortho phosphoric acid and melamine at a molar ratio of at least about 1.5:1, respectively.
2. A method according to claim 1 wherein the molar ratio of ortho phosphoric acid to melamine ranges from about 1.5 to about 2.5:1, respectively.
3. Melamine phosphate having hydrogen bonded thereto at least about 0.5 mole of ortho phosphoric acid per mole of melamine phosphate.
4. Melamine phosphate having hydrogen bonded thereto from about 0.5 to about 1.5 moles of ortho phosphoric acid per mole of melamine phosphate.
5. Melamine phosphate having hydrogen bonded thereto 0.6 mole of ortho phosphoric acid per mole of melamine phosphate.

* * * * *